United States Patent [19]

Iwamoto et al.

[11] Patent Number: 4,548,605
[45] Date of Patent: Oct. 22, 1985

[54] METHOD FOR MANUFACTURING PLASTIC CONTAINER CONTAINING INFUSION SOLUTION WHICH DOES NOT ALLOW DETERIORATION OF INFUSION SOLUTION FOR LONG PERIOD OF TIME

[75] Inventors: Tomiyuki Iwamoto, Tokyo; Naoki Hayakawa, Kashiwa; Haruo Honda, Kawasaki; Teppei Maruyama, Komae, all of Japan

[73] Assignee: Terumo Kabushiki Kaisha, Tokyo, Japan

[21] Appl. No.: 447,689

[22] Filed: Dec. 7, 1982

[30] Foreign Application Priority Data

Oct. 30, 1982 [JP] Japan .................. 57-191009

[51] Int. Cl.⁴ .................. B65D 81/24
[52] U.S. Cl. .................. 604/410; 206/438
[58] Field of Search .................. 604/403, 408, 410; 206/438, 440, 363, 370, 63.3; 435/253

[56] References Cited

U.S. PATENT DOCUMENTS

| | | | |
|---|---|---|---|
| 3,202,273 | 8/1965 | Riall .................. | 206/63.3 |
| 3,315,802 | 4/1967 | Lonholdt et al. .................. | 206/363 |
| 4,150,744 | 4/1979 | Fennimore .................. | 206/363 |
| 4,262,091 | 4/1981 | Cox .................. | 435/253 |
| 4,410,026 | 10/1983 | Boggs et al. .................. | 604/408 |

Primary Examiner—C. Fred Rosenbaum
Assistant Examiner—Michelle N. Lester
Attorney, Agent, or Firm—Frishauf, Holtz, Goodman & Woodward

[57] ABSTRACT

A plastic container containing an infusion solution which may not allow deterioration of the infusion solution over a long period of time, is prepared by providing a container which is made of a flexible plastic material having a heat resistance able to withstand heat of autoclaving sterilization and which holds an infusion solution containing components which may easily deteriorate upon contact with oxygen; the container is packaged with a first packaging material which consists of a plastic material having a gas permeability and a heat resistance able to withstand the heat of autoclaving sterilization. The container packaged with the first packaging material is sterilized by autoclaving in an atmosphere of saturated steam containing substantially no oxygen. The packaged and sterilized container is cooled while substantially maintaining a pressure of autoclaving sterilization by introducing an inert gas into the atmosphere. The container is further packaged with a second packaging material which has a high oxygen gas impermeability.

19 Claims, 3 Drawing Figures

METHOD FOR MANUFACTURING PLASTIC CONTAINER CONTAINING INFUSION SOLUTION WHICH DOES NOT ALLOW DETERIORATION OF INFUSION SOLUTION FOR LONG PERIOD OF TIME

BACKGROUND OF THE INVENTION

I. Field of the Invention

The present invention relates to a method for manufacturing a plastic container containing an infusion solution and, more particularly, to a method for manufacturing a plastic container containing an infusion solution which may not allow deterioration of the infusion solution held therein over a long period of time.

II. Description of the Prior Art

In order to prevent infection in hospitals during administration of an infusion solution for injection, closed systems are recently more often used which allow administration of such an infusion solution via a closed system without using an open cannula. A closed system of this type requires a flexible plastic container as a bag for holding an infusion solution in place of the conventional glass bottle or glass ampoule. The closed system utilizes the flexibility of the bag during fluid therapy.

A plastic container containing an infusion solution must be subjected to sterilization before use as must conventional containers. Sterilization is generally performed by autoclaving which is performed in saturated steam at a high temperature. A plastic material which has a low gas permeability at ambient temperature, such as polyvinyl chloride, has a high gas permeability during such autoclaving. Then, oxygen in the atmosphere is introduced into the container through the container wall thereby causing the infusion solution held therein to deteriorate. If the infusion solution contains components which easily deteriorate upon contact with oxygen, that is, if the infusion solution is, for example, a highly concentrated amino acid fluid or fat emulsion, it is subject to deterioration.

Even if the container is sterilized without causing such deterioration in the infusion solution, contamination of the container outer surface during storage may cause a hygiene problem during use.

SUMMARY OF THE INVENTION

It is an object of the present invention to provide a method for manufacturing a plastic container containing an infusion solution, which may not cause deterioration of the infusion solution either during or after sterilization, and which maintains the sterile condition of the container outer surface for a long period of time.

The above object of the present invention is achieved by a method for manufacturing a plastic container containing an infusion solution which may not allow deterioration of the infusion solution over a long period of time, comprising the steps of providing a container which is made of a flexible plastic material having a heat resistance able to withstand the heat of autoclaving sterilization and which holds the infusion solution containing components which may easily deteriorate upon contact with oxygen; packaging the container with a first packaging material which consists of a plastic material having a low gas permeability and a heat resistance able to withstand the heat of autoclaving sterilization; autoclaving sterilizing the packaged container in an atmosphere of saturated steam containing substantially no oxygen; cooling the packaged and sterilized container, while substantially maintaining the pressure of autoclaving sterilization by introducing an inert gas into the atmosphere; and further packaging the bag with a second packaging material having a high oxygen gas impermeability.

Autoclaving sterilization is generally performed at a temperature within a range of 100 to 130° C., and, especially, at a temperature within a range of 115 to 126° C., and at a gauge pressure of 1.2 to 2.0 kg/cm$^2$ of the atmosphere described above.

The inert gas which is introduced during cooling after sterilization is preferably nitrogen gas.

Packaging with the second Packaging material is preferably performed in a vacuum or in a nitrogen atmosphere.

The container is preferably made of polyvinyl chloride or a cross-linked ethylene-vinyl acetate copolymer.

The infusion solution includes, for example, at least one high-calory fluid component (i.e., a central venous nutrition component) such as a highly concentrated amino acid fluid containing tryptophan or a fat emulsion.

Examples of the first packaging material are a polypropylene film, a high-density polyethylene or a polyester film, or a laminate film consisting of an inner film of a non-stretched polypropylene and an outer film of a biaxially stretched polypropylene; and a laminate film consisting of an inner film of a non-stretched polypropylene, an intermediate film of a nylon, and an outer film of a biaxially stretched polypropylene.

The second packaging material preferably has an oxygen permeability of 0.1 or less {(cc cm/cm$^2$ see, cmHg)$\times 10^{12}$(35° C., dry)}. An example of such a material is a three-layered laminate film including a polyvinyl alcohol layer as the intermediate layer, or a laminate film including an aluminum layer.

Packaging with the first and second packaging materials is performed preferably by heat sealing; the second packaging material is preferably heat-sealed to a predetermined portion of the first packaging material.

A first notch may be formed in the heat-sealed portion of the first packaging material. A second notch may be formed in that portion of the heat-sealed portion of the second packaging material which corresponds to the first notch. The first and second packaging materials may then be opened along the first and second notches.

DETAILED DESCRIPTION OF THE PREFERRED EMBODIMENT

Figure 1A:
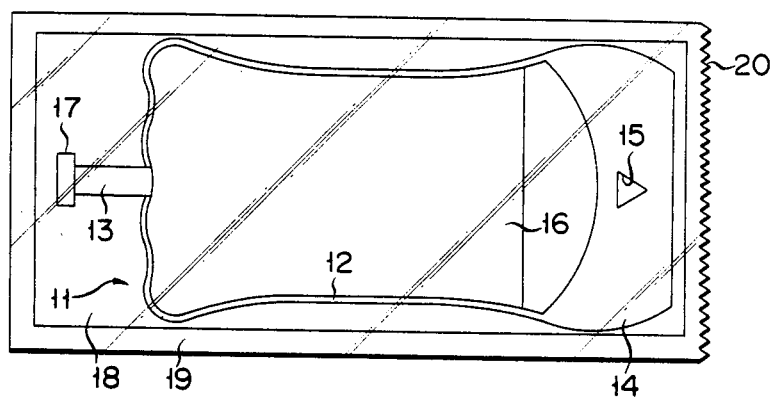
FIGS. 1A and 1B are plan views of plastic containers containing an infusion solution at different steps of the method of the present invention.

The present inventors have made extensive studies in an attempt to develop a method for manufacturing a plastic container containing an infusion solution which does not allow deterioration of the infusion solution either during or after sterilization and which maintains the sterile condition of the container outer surface over a long period of time. As a result of such studies, the present inventors have reached the following conclusions. First, if a plastic container containing an infusion solution is first packaged, and is then subjected to autoclaving sterilization, contact of the containers with the outer atmosphere (e.g., in checking the contents) does not interfere with the sterilized state of the container outer surface. Second, if autoclaving sterilization is performed in a saturated steam atmosphere containing substantially no oxygen, the infusion solution held in the container may not deteriorate during sterilization even if the container and/or the first packaging material permeate oxygen under sterilizing conditions. Finally, if the container is further packaged with the second packaging material having a high oxygen gas impermeability after cooling, the infusion solution may be kept without deteriorating for a longer period of time. Based on these findings, the present invention has been established.

An amino acid fluid may be determined not to have deteriorated if it has a transmission factor of 95% or higher for visible light of 420 nm wavelength and a dissolved oxygen content of 2 ppm or less after storage for 2 years. A fat emulsion may be determined not to have deteriorated if it does not exhibit any coloring notable by visual observation, does not contain any fat particles having particle diameters of 7 $\mu$m or more (microscope observation), and has a dissolved oxygen content of 2 ppm or less after storage for 2 years.

As has been described earlier, the container containing an infusion solution manufactured according to the present invention is subjected to autoclaving sterilization. For this reason, the container must be made of a flexible plastic material which has a heat resistance able to withstand the heat of autoclaving sterilization (that is, is not subject to melting, deformation, deterioration, degradation, etc.). Such a plastic material preferably has a low oxygen permeability at usual ambient temperatures (1 to 30° C.) The plastic container is preferably manufactured by heat sealing, especially, by high-frequency induction heating of plastic sheets or a flat tube. Therefore, the plastic material for the plastic container preferably has high-frequency sealability. In addition, the plastic material is preferably transparent or semi-transparent in order to allow visual observation of the infusion solution through the container wall.

Examples of a plastic material which satisfies these conditions include polyvinyl chloride, a cross-linked ethylene-vinyl acetate copolymer, and a high-density polyethylene. The ethylene-vinyl acetate (EVA) copolymer is cross-linked to a degree (gel content) of 50% or more by electron beams or $\gamma$-ray beams so as to provide a predetermined heat resistance. From the viewpoint of flexiblity, the EVA copolymer preferably has a vinyl acetate content of 10 to 20% by weight. Since the EVA copolymer can not be high-frequency welded after being cross-linked to the degree of 50% or more, a container is first formed from a non-crosslinked EVA copolymer and then cross-linked by radiation with electron beams or the like.

The infusion solution which contains components which easily deteriorate upon contact with oxygen may be at least one high-calory liquid component (central venous nutrition component) such as a high concentration (10 to 12% by weight) amino acid fluid containing tryptophan or a fat emulsion. The infusion solution may be prepared by a conventional method. The infusion solution may alternatively be a blood storing liquid.

The first packaging material for packing the plastic container holding the infusion solution before autoclaving sterilization must have gas permeability during autoclaving sterilization and must satisfy similar requirements to those of the plastic material of the container.

The first packaging material is a plastic material which has gas (oxygen gas and steam) permeability during autoclaving sterilization. Accordingly, oxygen which may have remained inside the plastic container or between the plastic container and the first packaging material may be exhausted into the sterilizing atmosphere with a low oxygen partial pressure through the first packaging material during autoclaving sterilization. Simultaneously, sterilization of the container can be satisfactorily performed by the introduction of high-temperature steam through the first packaging material. Even if the water content of the infusion solution is transferred to the surface of the plastic container through its wall, it is subsequently transferred to the surface of the first packaging material through its wall during cooling. Thus, water may not remain in the space between the plastic container and the first packaging material. It is noted that the first packaging material preferably exhibits a high gas impermeability at the ambient temperatures.

Preferred examples of the first packaging material include single-layer film, e.g., a polypropylene film, a high-density polyethylene film, and a polyester film; a laminate film consisting of a non-stretched polypropylene (CPP) film as an inner layer and a biaxially stretched polypropylene (OPP) film as an outer layer; and a laminate film consisting of a non-stretched polypropylene (CPP) film as an inner layer, a nylon film as an intermediate layer, and a biaxially stretched polypropylene (OPP) film as an outer layer. The first packaging material may comprise a plurality of separate films; packing is preferably performed by deep draw vacuum forming.

The second packaging material for further packaging the plastic container containing the infusion solution is preferably a material which has a high oxygen gas impermeability. The second packaging material preferably has an oxygen permeability of 0.1 {(cc cm/cm$^2$ see, cmHg)$\times 10^{12}$ (35° C., dry)} or less. In addition, the second packaging material preferably has good heat sealability.

Examples of such a material for the second packaging material include laminate films including a polyvinyl alcohol or aluminum layer. Since hydroxyl groups of polyvinyl alcohol are bonded with each other through hydrogen bonding, polyvinyl alcohol exhibits an extremely high impermeability (barrier property) to oxygen gas. In order to improve heat sealability of a polyvinyl alcohol film, it preferably has as an inner layer a plastic film having heat sealability such as a non-stretched polypropylene (CPP) film. In order to eliminate the adverse effects of water content in the external atmosphere on the polyvinyl alcohol film, the film preferably has another plastic film laminated thereon as an outer layer. Examples of such an outer layer include a biaxially stretched polypropylene (OPP) film, a polyester film, a biaxially stretched nylon film, and a polyvinylidene chloride film. A laminate film having such a polyvinyl alcohol film as an intermediate layer is commercially available, for example, as "Evar" from KURARAY CO., LTD. Examples of the laminate film having an aluminum film include a polyester film, a polypropylene film and a high-density polyethylene film each laminated with an outer aluminum layer.

The method of the present invention will now be described in more detail with reference to the accompanying drawings.

Referring to FIG. 1A, a flexible plastic container or bag 11 is made of the plastic material described above. The bag 11 may be prepared by, for example, superposing two suitable plastic sheets on top of each other and heat-sealing a periphery 12 of the laminate film. An infusion solution port 13 is formed at one end of the bag 11 to communicate with the interior thereof, through which the infusion solution 16 is supplied. The bag 11 may have a relatively wide sealed portion 14 at its other end. A suspension hole 15 for suspending the bag 11 from a suitable support member can be formed at this sealed portion 14.

After the infusion solution 16 is supplied into the bag 11, the bag 11 is sealed with a sealing member 17 by heat sealing, high-frequency welding or the like.

The bag 11 now containing the infusion solution 16 is packed inside the first packaging material 18, and is preferably vacuum-packed therein. The first packaging material 18 is applied by, for example, superposing two plastic films sandwiching the bag 11 therebetween and sealing a periphery of the two films to form a heat-sealed portion 19. At least one notch 20 is preferably formed at at least one edge of the heat-sealed portion 19.

Figure 2:
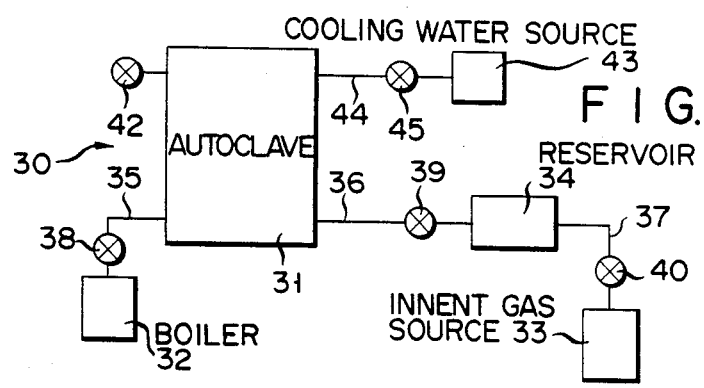
FIG. 2 is a schematic view showing a sterilization apparatus which may be used in the method of the present invention.

Subsequently, the packaged plastic bag containing the infusion solution as shown in Fig. 1A is subjected to autoclaving sterilization in an atmosphere of saturated steam which contains substantially no oxygen. Autoclaving sterilization can be performed by an apparatus 30 as shown in FIG. 2.

The apparatus 30 has an autoclave 31 to perform sterilization. One end of the autoclave 31 is connected to a steam source such as a boiler 32 through a line 35 via a valve 38. A source 33 of a gas which is inert to the infusion solution, preferably nitrogen gas, is connected to the other end of the autoclave 31 through a line 37, a valve 40, an inert gas reservoir 34, a line 36 and a valve 39. The reservoir 34 may be omitted (in which case, the line 36 and the valve 39 may also be omitted.) An exhaust valve 42 is also connected to the autoclave 31. A cooling water source 43 is also connected to the autoclave 31 through a line 44 and a valve 45.

In order to perform autoclaving sterilization, a plurality of packaged plastic bags containing the infusion solution are first placed in the autoclave 31. Steam is introduced into the autoclave 31 from the boiler 32 for a predetermined time interval (e.g., 2 to 10 minutes) to exhaust substantially all the oxygen or air inside the autoclave 31 through the exhaust valve 42. The exhaust valve 42 is then closed. Steam at a predetermined temperature is further introduced into the autoclave 31 from the boiler 32 to a saturation level in order to perform sterilization. The saturated steam temperature during sterilization is generally 100° to 130° C. and typically 115° to 126° C. The sterilization time is 10 to 40 minutes. The gauge pressure in the autoclave during sterilization is about 1.2 to 2.0 kg/cm$^2$. In order to obtain this pressure during sterilization, the inert gas is introduced into the autoclave 31 in a suitable amount from the source 33 through the valve 40.

After sterilization, cooling water is introduced in a suitable amount from the cooling water source 43 into the autoclave 31 to sufficiently cool the infusion solution held in the bag. Packaging with the second packaging material is preferably performed as soon as the bag is taken out from the autoclave 31. If the second packaging material 21 is a laminate film having a polyvinyl alcohol film, the bag must be sufficiently cooled (e.g., 40° C. or lower) inside the autoclave 31 because polyvinyl alcohol has a poor heat resistance. In any case, the pressure in the autoclave 31 is relatively abruptly decreased, whereas the infusion solution does not cool so quickly. Therefore the bag may be damaged or broken by the pressure of the still hot infusion solution. In order to prevent this, the sterilization pressure in the autoclave 31 must be substantially maintained during cooling. In order to accomplish this, the inert gas is introduced from the source 33 into the autoclave 31 according to the present invention. After the infusion solution is sufficiently cooled, the gas inside the autoclave 31 is exhausted through the exhaust valve 42 to the normal pressure.

Figure 1B:
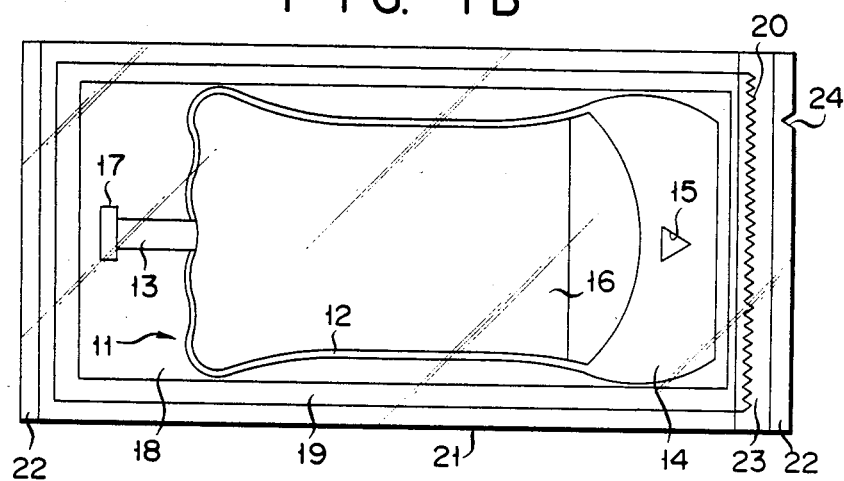

After the infusion solution is sufficiently cooled, the bag is taken out of the autoclave 31 and is wiped or dried to remove any water on the surface of the first packaging material 18. The bag is then further packaged with the second packaging material. Packaging with the second packaging material 21 is preferably performed in an atmosphere containing substantially no oxygen to allow substantially no oxygen to be trapped inside the second packaging material. Packaging with the second packaging material is, therefore, preferably performed by vacuum packing or in an inert gas (such as nitrogen) atmosphere. In packaging, two plastic sheets are superposed together and a periphery of the sheets is heat-sealed. Alternatively, two ends 22 of a tubular sheet 21 are heat-sealed to form heat-sealed portions 22, as shown in Fig. 1B. The heat-sealed portions 22 of the second packaging material 21 are formed at a distance from the first packaging material 18. Preferably, at a portion at which the second packaging material overlaps the heat-sealed portion 19 of the first packaging material 18 with the notch 20 formed therein the first and second packaging materials 18 and 21 are heat-sealed together to form a commonly sealed portion 23. The commonly sealed portion 23 is formed prior to forming the heat-sealed portions 22 of the second packaging material 21. A notch 24 may be formed in the heat-sealed portion 22 at a position corresponding to the notch 20, so that the two packaging materials may be simultaneously opened.

EXAMPLE 1

A 12% amino acid fluid (containing tryptophan) was prepared by the known method and was filled into a flexible polyvinyl chloride bag. The bag was then vacuum-packed with a two-layer laminate film consisting of a biaxially stretched polypropylene film having a thickness of 30μ as an outer layer and a non-stretched polypropylene film having a thickness of 20μ as an inner layer. The packaged bag was sterilized in a similar manner as has been described with reference to FIG. 2, and was cooled. Sterilization was performed at 115° C. for 30 minutes. After cooling, the bag sample was taken out of the autoclave. After wiping water drops off from the surface of the first packaging material, the bag was further packaged with a second packaging material which was a three-layer laminate film consisting of a polyvinylidene film having a thickness of 20μ as an outer film, a polyvinyl alcohol film having a thickness of 20μ as an intermediate film, and a non-stretched polypropylene film having a thickness of 20μ as an inner layer. In this case, after performing common heat sealing as shown in FIG. 1B, the bag was subjected to vacuum packing with a pillow packing machine. In this manner, a plastic bag containing an infusion solution packed inside two packaging materials was obtained which did not rupture during manufacture.

Comparative Example

A plastic bag containing an infusion solution packed inside one packaging material was prepared in a similar manner to that in Example 1 except that packaging with the second packaging material was not performed.

EXAMPLE 2

A plastic bag containing an infusion solution was packed inside two packaging materials in a similar manner to that in Example 1 except for the structures and materials of the packaging materials. The first packaging material consisted of a top material and a bottom material and was deep draw vacuum-formed. The top material was a two-layer laminate film consisting of a biaxially stretched polypropylene film having a thickness of $30\mu$ as an outer film and a non-stretched polypropylene film having a thickness of $30\mu$ as an inner layer. The bottom material was a three-layer laminate film consisting of a a biaxially stretched polypropylene film having a thickness of $30\mu$ as an outer layer, a nylon film having a thickness of $30\mu$ as an intermediate layer, and a non-stretched polypropylene film having a thickness of $30\mu$ as an inner layer. The second packaging material was a three-layer laminate film consisting of a biaxially stretched polypropylene film having a thickness of $20\mu$ as an outer layer, a polyvinyl alcohol film having a thickness of $15\mu$ as an intermediate film, and a non-stretched polypropylene film having a thickness of $50\mu$.

In order to examine the storage stability of the infusion solutions contained in the bags obtained in Examples 1 and 2 and the Comparative Example, the bags were subjected to an accelerated test in air. The transmission factor (%) of visible light having a 420 nm wavelength and the dissolved oxygen content (ppm) of the infusion solutions were tested. The obtained results are shown in Table below:

TABLE

|  | 40° C. for 2 weeks | | | 60° C. for 2 months | | |
| --- | --- | --- | --- | --- | --- | --- |
|  | Comparative example | Example 1 | Example 2 | Comparative example | Example 1 | Example 2 |
| Transmission factor (%) | 35.6 | 97.3 | 98.5 | Measurement impossible due to browning | 96.1 | 98.0 |
| Dissolved oxygen content (ppm) | 8.3 | 0.8 | 0.5 | 8.4 | 0.7 | 0.6 |

According to the present invention, autoclaving sterilization of the plastic container containing the infusion solution is performed after packaging the bag with the first packaging material. Therefore, contact with the ambient atmosphere after sterilization does not result in contamination of the plastic container. Since sterilization is performed in saturated steam containing substantially no oxygen, the infusion solution may not be brought into contact with oxygen during sterilization and may not therefore deteriorate. Cooling after sterilization is performed at a pressure substantially the same as the sterilization pressure, so that the plastic container may not be damaged or broken and the infusion solution may not deteriorate owing to the absence of oxygen. Since the plastic container is further packaging with the second packing material having a high oxygen gas barrier property, storage of the container over a long period of time does not allow contact of the infusion solution with ambient air. The infusion solution does not therefore deteriorate. Especially when the packaging with the second packaging material is performed in an atmosphere containing substantially no oxygen, deterioration of the infusion solution may be prevented further. Accordingly, the present invention provides a plastic container containing an infusion solution which may not allow deterioration of the infusion solution for a long period of time.

What we claim is:

1. A method for manufacturing a plastic container containing an infusion solution which does not allow deterioration of the infusion solution over a long period of time, comprising the steps of:

providing a container which is made of a flexible plastic material having a heat resistance able to withstand heat of autoclaving sterilization and which holds an infusion solution containing components which may easily deteriorate upon contact with oxygen;

packaging the container hermetically within a first plastic packaging material having oxygen gas and steam permeabilities during autoclaving sterilization, and also having a heat resistance able to withstand the heat of autoclaving sterilization;

autoclaving sterilizing the container packaged in the first packaging material in an atmosphere of saturated steam containing substantially no oxygen by introducing the saturated steam through the first packaging material;

cooling the packaged and sterilized container, while substantially maintaining a pressure of autoclaving sterilization by introducing an inert gas into the atmosphere; and further packaging the container, which is already packaged in said first packaging material, within a second packaging material which completely surrounds said first packaging material, said second packaging material having a high oxygen gas impermeability, said further packaging step being carried out without introducing an atmosphere surrounding the first packaging material into the space between the container and the first packaging material.

2. A method according to claim 1, wherein said autoclaving sterilization is performed at a temperature of 100° to 130° C.

3. A method according to claim 1, wherein said autoclaving sterilization is performed at a temperature of 115° to 126° C. and a gauge pressure of 1.2 to 2.0 kg/cm$^2$.

4. A method according to claim 1, wherein said inert gas is nitrogen gas.

5. A method according to claim 4, wherein said step of further packaging with the second packaging material is performed by vacuum packing.

6. A method according to claim 4, wherein said step of further packaging with the second packaging material is performed in a nitrogen atmosphere.

7. A method according to claim 1, wherein the container is made of polyvinyl chloride or a cross-linked ethylene-vinyl acetate copolymer.

8. A method according to claim 1, wherein the infusion solution is a high-calory fluid component.

9. A method according to claim 8, wherein the infusion solution is an amino acid fluid containing tryptophan.

10. A method according to claim 8, wherein the infusion solution is a fat emulsion.

11. A method according to claim 1, wherein the first packaging material is a member selected from the group consisting of polypropylene, high-density polyethylene, and high-density polyester.

12. A method according to claim 1, wherein the first packaging material is a member selected from the group consisting of a laminate film having a non-stretched polypropylene film as an inner layer and a biaxially stretched polypropylene film as an outer film, and a laminate film having a non-stretched polypropylene film as an inner layer, a nylon film as an intermediate film and a biaxially stretched polyethylene film as an outer film.

13. A method according to claim 1, wherein the second packaging material has an oxygen permeability of not greater than 0.1 $\{(cc\ cm/cm^2\ sec, cmHg) \times 10^{12}\ (35°\ C., dry)\}$.

14. A method according to claim 13, wherein the second packaging material is a three-layer laminate film having a polyvinyl alcohol film as an intermediate layer.

15. A method according to claim 13, wherein the second packaging material is a laminate film consisting of a polyester film, a polypropylene film or a high-density polyethylene film with an aluminum film.

16. A method according to claim 1, wherein said packaging with the first and second packaging materials is performed by heat sealing, and the second packaging material is heat-sealed to a predetermined portion of the first packing material.

17. A method according to claim 16, wherein a first notch is formed in a heat-sealed portion of the first packing material, and a second notch is formed at a position in a heat-sealed portion of the second packing material corresponding to the first notch, thereby facilitating simultaneous opening of the first and second packing materials along the first and second notches.

18. A double packaged plastic container containing an infusion solution manufactured by a method according to claim 1, and comprising a container which is made of a flexible plastic material having a heat resistance able to withstand heat of autoclaving sterilization and which holds the infusion solution containing components which easily deteriorate upon contact with oxygen; a first packaging material packaging the container and consisting of a plastic material having a gas permeability and a heat resistance able to withstand the heat of autoclaving sterilization; and a second packaging material further packaging the container packaged with the first packaging material and having a high oxygen gas impermeability.

19. A method according to claim 7, wherein the cross-linked ethylene-vinyl acetate copolymer has a gel content of 50% or more and a vinyl acetate content of 10 to 20% by weight.

* * * * *